US012582438B2

(12) United States Patent
Waterbury

(10) Patent No.: US 12,582,438 B2
(45) Date of Patent: *Mar. 24, 2026

(54) COMPUTER-ASSISTED TELE-OPERATED SURGERY SYSTEMS AND METHODS

(71) Applicant: Intuitive Surgical Operations, Inc., Sunnyvale, CA (US)

(72) Inventor: Andrew Cullen Waterbury, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 17/887,802

(22) Filed: Aug. 15, 2022

(65) Prior Publication Data

US 2023/0023504 A1 Jan. 26, 2023

Related U.S. Application Data

(63) Continuation of application No. 16/314,207, filed as application No. PCT/US2017/039732 on Jun. 28, 2017, now Pat. No. 11,413,064.

(Continued)

(51) Int. Cl.
*A61B 17/34* (2006.01)
*A61B 17/02* (2006.01)
(Continued)

(52) U.S. Cl.
CPC ...... *A61B 17/3421* (2013.01); *A61B 17/0281* (2013.01); *A61B 34/30* (2016.02);
(Continued)

(58) Field of Classification Search
CPC . A61B 17/3421; A61B 17/0281; A61B 34/30; A61B 2017/3443; A61B 2017/3484; A61B 2034/302
See application file for complete search history.

(56) References Cited

U.S. PATENT DOCUMENTS 5,882,344 A  3/1999  Stouder, Jr.
6,613,062 B1 *  9/2003  Leckrone ........... A61B 17/3478
606/167

(Continued)

FOREIGN PATENT DOCUMENTS

KR  101439228 B1  10/2014
KR  20150127114 A  11/2015
WO  WO-2007093957 A2 *  8/2007  ......... A61B 17/3421

OTHER PUBLICATIONS

International Search Report and Written Opinion for Application No. PCT/US2017/039732, mailed on Oct. 18, 2017, 15 pages.
(Continued)

*Primary Examiner* — Sarah A Long
(74) *Attorney, Agent, or Firm* — Jones Burke, PLLC

(57) ABSTRACT

Systems and methods for minimally invasive computer-assisted telesurgery are described. For example, this disclosure describes cannula devices for use with computer-assisted teleoperated surgery systems. The cannula devices can facilitate enlargement of a minimally invasive surgical workspace by creating a tissue tent. The devices and methods described herein can be used in conjunction with computer-assisted teleoperated surgery systems that use either hardware-constrained remote centers of motion or software-constrained remote centers of motion.

14 Claims, 11 Drawing Sheets

Related U.S. Application Data

(60) Provisional application No. 62/357,745, filed on Jul. 1, 2016.

(51) Int. Cl.
    *A61B 34/30*        (2016.01)
    *A61B 90/00*        (2016.01)

(52) U.S. Cl.
    CPC ................. *A61B 2017/3443* (2013.01); *A61B 2017/3484* (2013.01); *A61B 2034/302* (2016.02); *A61B 2090/371* (2016.02)

(56) References Cited

U.S. PATENT DOCUMENTS

| | | | |
|---|---|---|---|
| 9,681,889 B1 | 6/2017 | Greenhalgh et al. | |
| 11,413,064 B2 | 8/2022 | Waterbury | |
| 2007/0038216 A1 | 2/2007 | Hamada | |
| 2007/0078463 A1 | 4/2007 | Malandain | |
| 2011/0071544 A1 | 3/2011 | Steger et al. | |
| 2014/0046299 A1* | 2/2014 | Shelton, IV ....... | A61B 17/3439 604/513 |
| 2017/0105811 A1* | 4/2017 | Garbus ................. | A61B 34/30 |
| 2018/0098789 A1 | 4/2018 | White et al. | |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

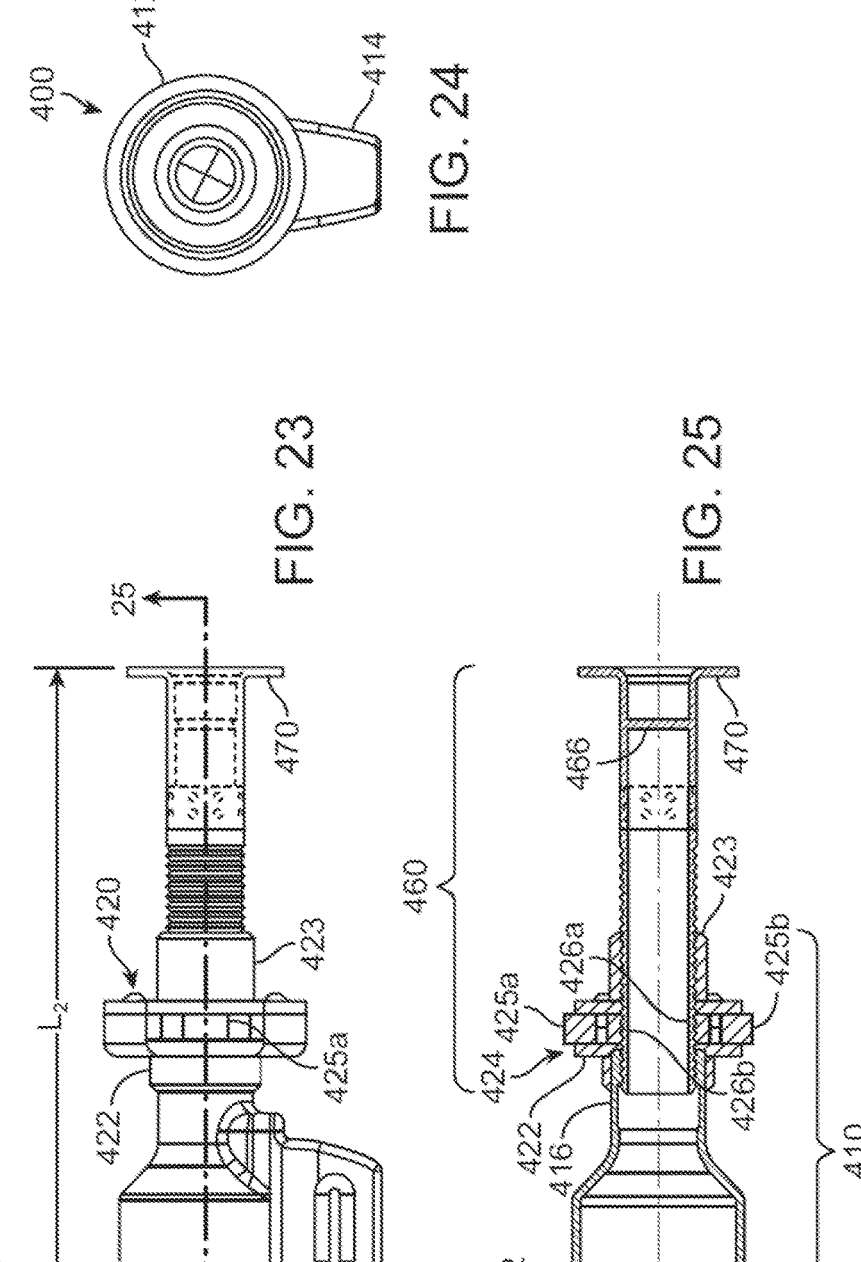

COMPUTER-ASSISTED TELE-OPERATED SURGERY SYSTEMS AND METHODS

CROSS REFERENCE TO RELATED APPLICATIONS

This application is a continuation of U.S. application Ser. No. 16/314,207 filed Dec. 28, 2018, and issued as U.S. Pat. No. 11,413,064, which is a National Stage Application under 35 U.S.C. § 371 and claims the benefit of International Application No. PCT/US2017/039732 filed Jun. 28, 2017, which claims the benefit of U.S. Provisional Application No. 62/357,745, filed Jul. 1, 2016. The disclosure of the prior applications are considered part of and are incorporated by reference in the disclosure of this application.

TECHNICAL FIELD

This disclosure relates to devices and methods for minimally invasive computer-assisted teleoperated surgery. For example, this disclosure relates to computer-assisted teleoperated surgery cannula devices that can facilitate enlargement of a minimally invasive surgical workspace by creating a tissue tent.

BACKGROUND

Robotic systems and computer-assisted devices often include robot or movable arms to manipulate instruments for performing a task at a work site and at least one robot or movable arm for supporting an image capturing device which captures images of the work site. A robot arm comprises a plurality of links coupled together by one or more actively controlled joints. In many embodiments, a plurality of actively controlled joints may be provided. The robot arm may also include one or more passive joints, which are not actively controlled but comply with movement of an actively controlled joint. Such active and passive joints may be revolute or prismatic joints. The configuration of the robot arm may then be determined by the positions of the joints and knowledge of the structure and coupling of the links.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often avoiding the trauma generally associated with accessing a surgical worksite by open surgery techniques. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

SUMMARY

This disclosure provides devices and methods for minimally invasive robotic surgery using a computer-assisted teleoperated medical device. For example, this disclosure provides computer-assisted teleoperated surgery cannula devices that can facilitate enlargement of a minimally invasive surgical workspace by creating a tissue tent. The devices and methods provided herein can be used in conjunction with robotic surgery systems that use either hardware-constrained remote centers of motion or software-constrained remote centers of motion.

In one implementation, a cannula assembly for use with a computer-assisted teleoperated surgery system includes a proximal (located away from a surgical site) cannula portion configured to be releasably coupled to a robotic surgery manipulator arm, and a distal (located towards a surgical site) cannula portion adjustably engageable with the proximal cannula portion. The proximal cannula portion defines a longitudinal axis and a central lumen configured for slidably receiving a surgical instrument. The distal cannula portion includes a body wall retractor. The distal cannula portion and the proximal cannula portion together define, as engaged, an overall assembly length along the longitudinal axis. The overall assembly length is adjustable during use.

Such a cannula assembly for use with a computer-assisted teleoperated surgery system may optionally include one or more of the following features. The proximal cannula portion may include a user-actuatable adjustment mechanism. Actuation of the user-actuatable adjustment mechanism may allow the cannula assembly to be reconfigured between a first configuration and a second configuration that have differing overall assembly lengths. The user-actuatable adjustment mechanism may include a ball that is spring-biased into engagement with a groove. Actuation of the user-actuatable adjustment mechanism may allow the ball to disengage from the groove. The user-actuatable adjustment mechanism may include a tooth that is spring biased into engagement with a groove. Actuation of the user-actuatable adjustment mechanism may allow the tooth to disengage from the groove. The element configured to engage with and retract the body wall may include a flange. The flange may be reconfigurable between an expanded unrestrained size and a smaller constrained size. The smaller constrained size may be used while inserting the element configured to engage with and retract the body wall through an incision in the body wall. The flange may be resilient such that the flange self-reconfigures to the expanded unrestrained size upon removal of size-constraining forces. The cannula assembly may be user-adjustable into three or more different configurations that each define a different overall assembly length. The distal cannula portion may include a lumen configured for slidably receiving the surgical instrument. The distal cannula portion may include a seal within the lumen. The seal may be configured to provide a seal around an outer periphery of a shaft of the surgical instrument.

In another implementation, a computer-assisted teleoperated surgery system includes a robotic surgery manipulator arm mounted to a base; a surgical instrument movably coupled to the robotic surgery manipulator arm; and a cannula assembly. The cannula assembly includes a proximal cannula portion configured to be releasably coupled to the robotic surgery manipulator arm, and a distal cannula portion adjustably engageable with the proximal cannula portion. The proximal cannula portion defines a longitudinal axis and a central lumen configured for slidably receiving the surgical instrument. The distal cannula portion includes a body wall retractor. The distal cannula portion and the proximal cannula portion together define, as engaged, an overall assembly length along the longitudinal axis. The overall assembly length is adjustable during use.

Such a computer-assisted teleoperated surgery system may optionally include one or more of the following features. The system may include a plurality of the robotic surgery manipulator arms, a plurality of the surgical instruments, and a plurality of the cannula assemblies.

In another implementation, a method of operating a computer-assisted teleoperated surgery system includes inserting a distal end portion of a cannula assembly through a body wall incision such that an element of the distal end portion that is configured to engage with and retract the body wall is positioned in a surgical working space below the body wall; coupling a proximal end portion of the cannula assembly to the distal end portion of the cannula assembly; coupling the proximal end portion of the cannula assembly to a robotic surgery manipulator arm; and adjusting the cannula assembly from a first configuration in which the cannula assembly has a first overall longitudinal length into a second configuration in which the cannula assembly has a second overall longitudinal length that is shorter than the first overall longitudinal length. The adjusting displaces the body wall such that the surgical working space is enlarged.

Such a method of operating a computer-assisted teleoperated surgery system may optionally include one or more of the following features. The adjusting may include actuating a latching mechanism of the cannula assembly. The element of the distal end portion that is configured to engage with and retract the body wall may include a flange. During the inserting, the flange may be configured in a diametrically small constrained size by the application of a size-constraining force, and after the inserting, the flange may self-reconfigure to a diametrically expanded unrestrained size upon removal of the size-constraining force. The method may also include coupling a surgical instrument to the robotic surgery manipulator arm and inserting a shaft of the surgical instrument through a lumen defined by the cannula assembly such that an end effector of the surgical instrument is positioned in the surgical working space. The method may also include coupling an endoscope to the robotic surgery manipulator arm and inserting a shaft of the endoscope through a lumen defined by the cannula assembly such that an image-capturing element of the endoscope is positioned in the surgical working space. In some cases, the method may be used during an arthroscopic surgery.

Some or all of the embodiments described herein may provide one or more of the following advantages. In some cases, the robotic surgery devices and methods provided herein facilitate tenting of the body wall through which the surgical access incision is made. Such devices provide various advantages, such as better visibility in the surgical working space. More room in the working space for better access is also facilitated by using the tenting methods provided herein. The devices and methods for tenting of the body wall may have advantages over insufflation in some cases. For example, while insufflation facilitates generally symmetrical enlargement of the surgical working space, tenting can facilitate asymmetrical enlargement of the surgical working space in some cases. For surgical working spaces that are shallow, or that have the entry point and operative points close together, asymmetrical enlargement can result in greater enlargement of the surgical working space than symmetrical enlargement.

The details of one or more embodiments are set forth in the accompanying drawings and the description below.

Other features, objects, and advantages will be apparent from the description and drawings, and from the claims.

BRIEF DESCRIPTION OF THE DRAWINGS

FIG. 22 is a side view of the cannula assembly of FIG. 15. In this view, the distal cannula portion is in a retracted arrangement in relation to the proximal cannula portion.

FIG. 23 is another side view of the cannula assembly of FIG. 22.

FIG. 24 is a proximal end view of the cannula assembly of FIG. 22.

FIG. 25 is a longitudinal cross-sectional view of the cannula assembly of FIG. 22.

Like reference symbols in the various drawings indicate like elements.

DETAILED DESCRIPTION

Figures 1, 2:
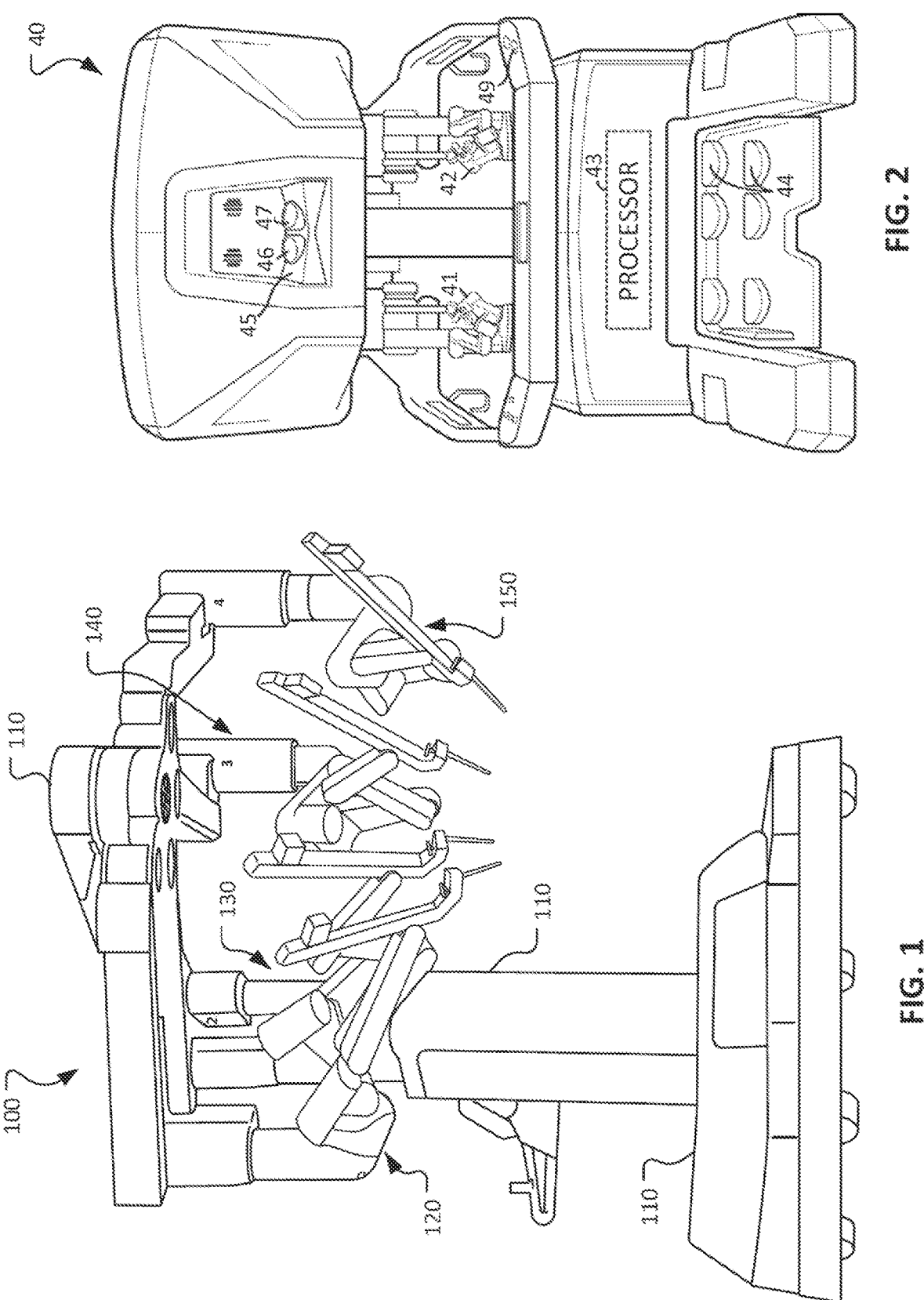
FIG. 1 is a perspective view of an example patient-side cart of a computer-assisted tele-operated surgery system.
FIG. 2 is a front view of an example surgeon console of a computer-assisted tele-operated surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length, and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Aspects of the invention are described primarily in terms of an implementation using a da Vinci® Surgical System, commercialized by Intuitive Surgical, Inc. of Sunnyvale, California. Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely exemplary and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, a surgical instrument having an 8 mm shaft diameter cannot simply be scaled down to a 5 mm shaft diameter due to mechanical, material property, and manufacturing considerations. Likewise, a 5 mm shaft diameter device cannot simply be scaled down to a 3 mm shaft diameter device. Significant mechanical concerns exist as physical dimensions are reduced.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

This disclosure provides improved surgical and robotic devices, systems, and methods. The inventive concepts are particularly advantageous for use with computer-assisted teleoperated surgical systems (which may be referred to as "surgical robotic systems") in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators to inhibit interference or collisions between these moving structures, and the like.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both.

When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

Referring to FIGS. 1 and 2, systems for minimally invasive computer-assisted telesurgery (also referred to herein as "minimally invasive robotic surgery") can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although described as a processor, it is to be appreciated that the processor 43 may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processor 43 may also be distributed as subunits throughout the telesurgery system.

Figure 3:
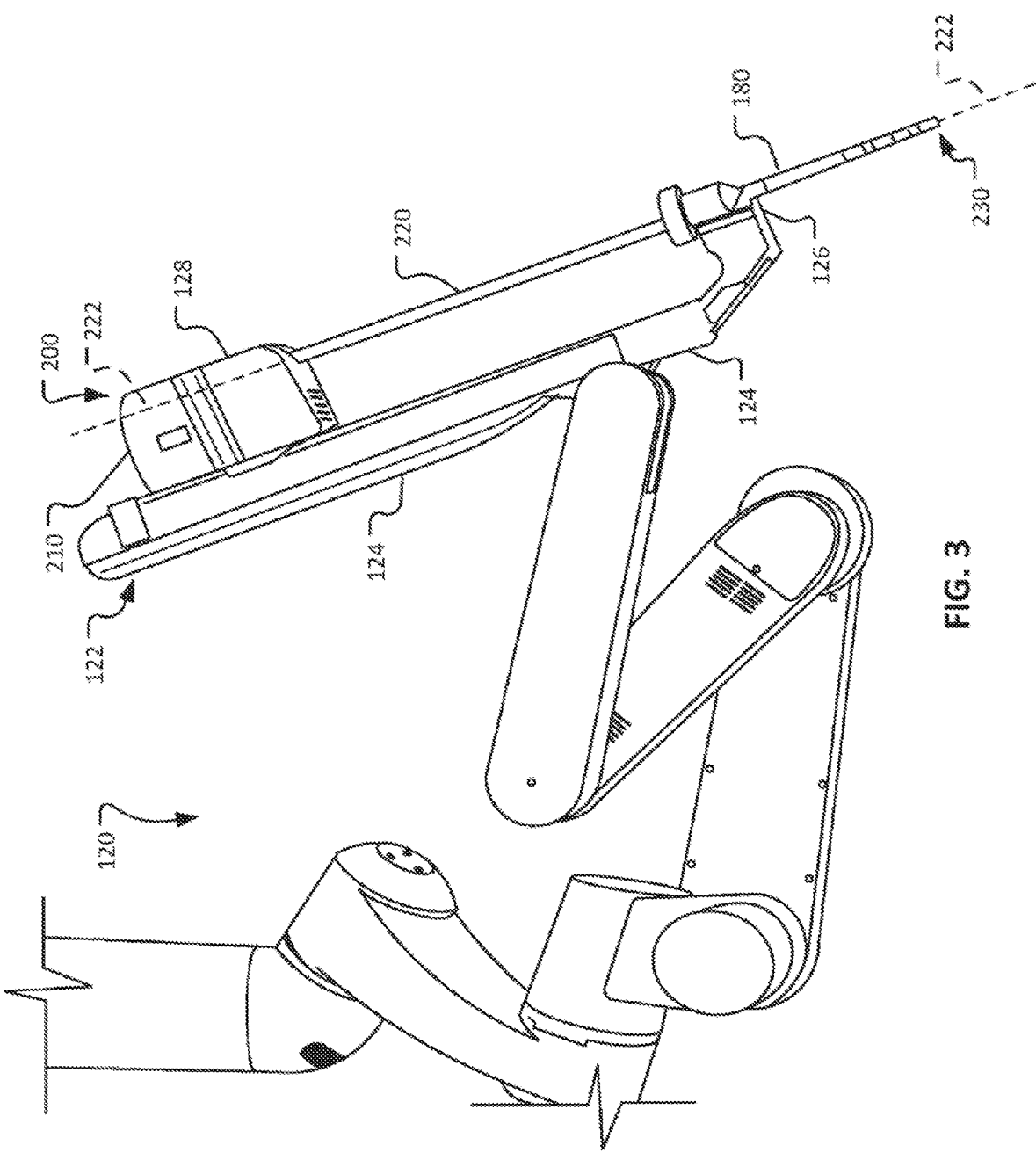
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably couple-able with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
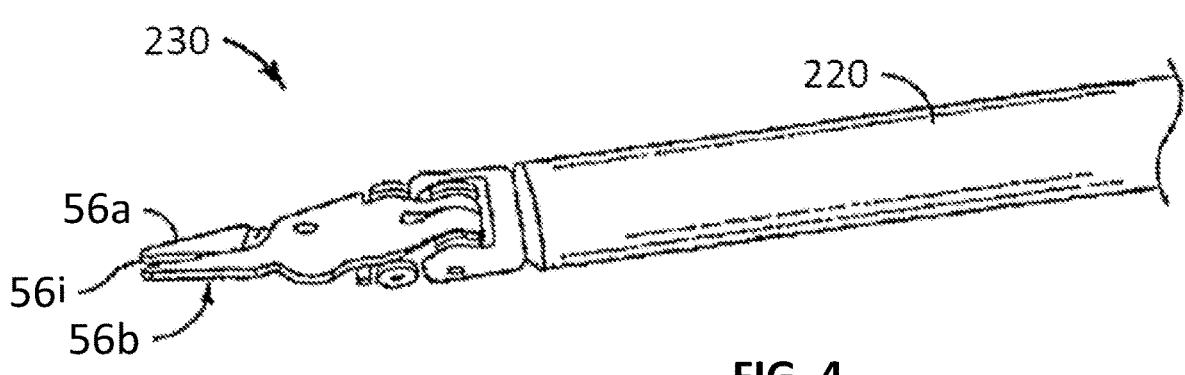
FIG. 4 is a perspective view of a distal end portion of an example surgical instrument in a first configuration.
Figure 5:
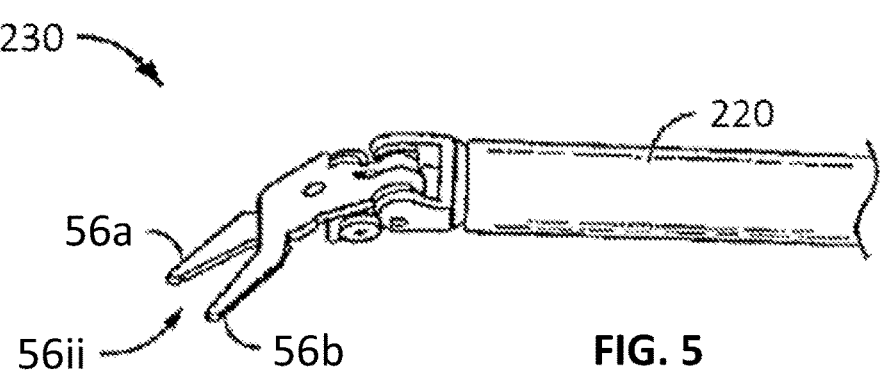
FIG. 5 is a perspective view of the distal end portion of the surgical instrument of FIG. 4 in a second configuration.
Figure 6:
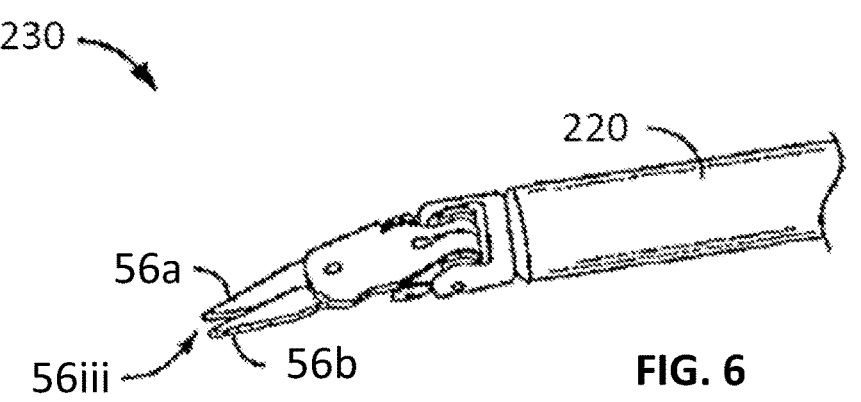
FIG. 6 is a perspective view of the distal end portion of the surgical instrument of FIG. 4 in a third configuration.

Also referring to FIGS. 4-6, a variety of alternative robotic surgical instruments of different types and differing end effectors 230 may be used, with the instruments of at least some of the manipulators being removed and replaced during a surgical procedure. Several of these end effectors, including, for example, DeBakey Forceps 56i, microforceps 56ii, and Potts scissors 56iii include first and second end effector elements 56a, 56b which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42.

The elongate shaft 220 allow the end effector 230 and the distal end of the shaft 220 to be inserted distally into a surgical worksite through a minimally invasive aperture (via cannula 180), often through a body wall (e.g., abdominal wall) or the like. In some cases, a body wall retractor member on a distal end of the cannula 180 can be used to tent the body wall, thereby increasing the surgical work-space size. In some cases, the surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 50. Hence, the robotic manipulator arm assemblies 120, 130, 140, and 150 will often undergo significant movement outside patient during a surgical procedure.

Figures 7, 8, 9:
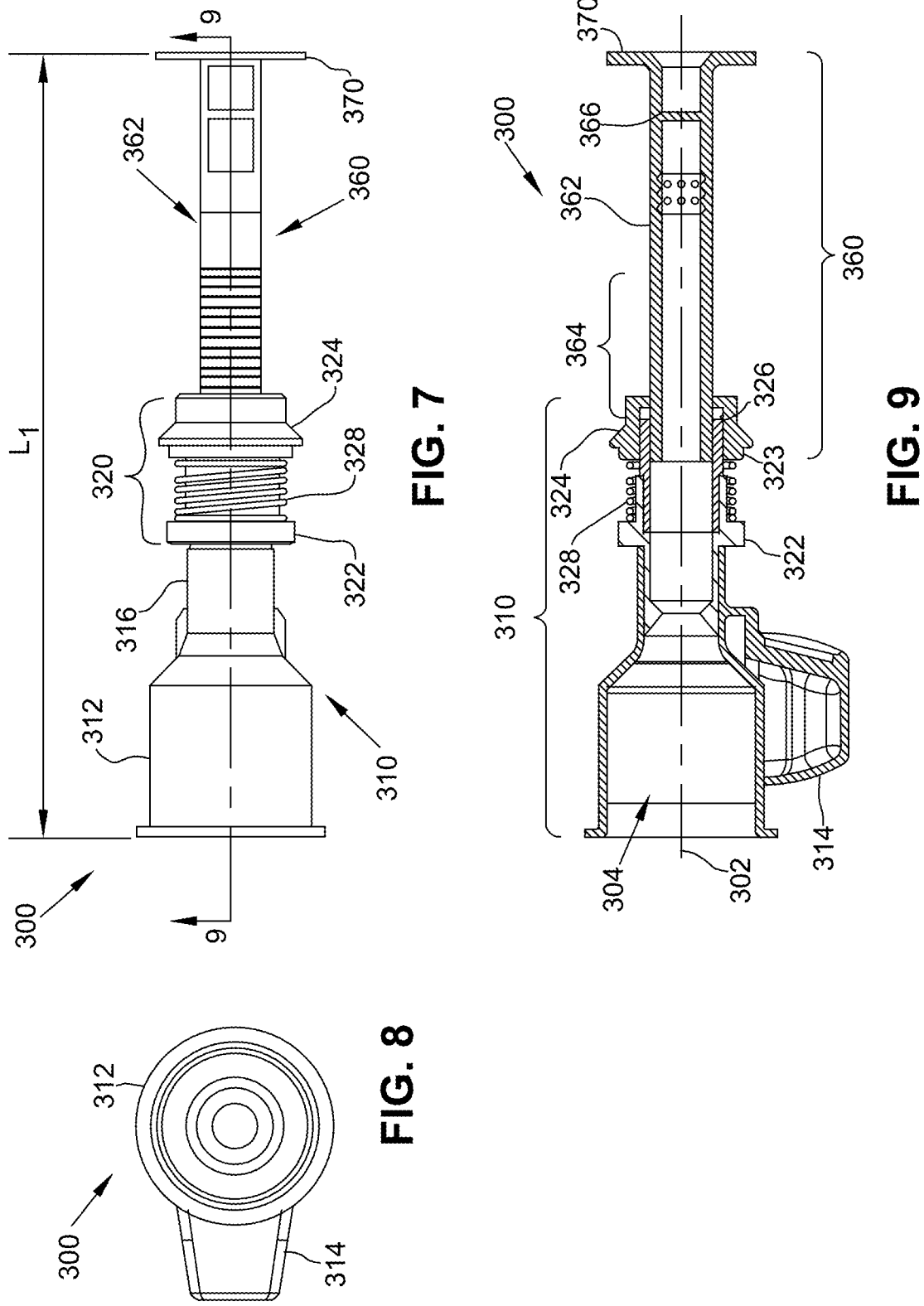
FIG. 7 is a side view of an exemplary cannula assembly with a flanged distal end for facilitating creation of a tissue tent during robotic surgery. The cannula assembly includes a proximal cannula portion and a distal cannula portion. In this view, the distal cannula portion is in an extended arrangement in relation to the proximal cannula portion.
FIG. 8 is a proximal end view of the cannula assembly of FIG. 7.
FIG. 9 is a longitudinal cross-sectional view of the cannula assembly of FIG. 7.

Referring to FIGS. 7-9, an example cannula assembly 300 includes a proximal cannula portion 310 and a distal cannula portion 360. In some cases, the cannula assembly 300 may also be referred to as a "trocar." The cannula assembly 300 defines a longitudinal axis 302 and a lumen 304 extending longitudinally through each of the proximal cannula portion 310 and the distal cannula portion 360. The lumen 304 is configured to slidably receive the shaft of a surgical instru-ment, such as the surgical instrument 200 described above.

In the depicted embodiment, the distal cannula portion 360 is adjustably engaged with the proximal cannula portion 310. That is, as described further below, the position of the distal cannula portion 360 in relation to the proximal can-nula portion 310 is user-adjustable. Such adjustability of the distal cannula portion 360 in relation to the proximal can-nula portion 310 facilitates the ability to adjust the overall longitudinal length of the cannula assembly 300 and to tent a body wall, as described further below.

Proximal cannula portion 310 includes a cannula bowl 312, an attachment member 314, a throat 316, and a user-actuatable adjustment mechanism 320. In some embodi-ments, the cannula bowl 312, the attachment member 314, and the throat 316 can be constructed like a conventional cannula for robotic surgery. The attachment member 314 is configured to releasably couple with the cannula clamp 126 (FIG. 3). The adjustment mechanism 320 is coupled to the throat 316.

In the depicted embodiment, the user-actuatable adjust-ment mechanism 320 includes a stationary collar 322, a sliding collar 324, one or more detent balls 326, and a spring 328. The stationary collar 322 is coupled to the throat 316. The sliding collar 324 surrounds a portion of the stationary collar 322 and is free to slide longitudinally in relation to the stationary collar 322. The one or more detent balls 326 are in contact with the inner diameter of the sliding collar 324. The spring 328 is disposed between the stationary collar 322 and the sliding collar 324. The spring 328 provides a force that acts to separate the sliding collar 324 distally away from the stationary collar 322.

In the depicted embodiment, the stationary collar 322 includes a distal sleeve 323. In some embodiments, the distal sleeve 323 can be made of a material that provides low sliding friction in relation to the sliding collar 324. For example, in some embodiments the distal sleeve 323 can be made of metallic materials such as, but not limited to, bronze, brass, stainless steel, impregnated metals, coated metals, and the like. In some embodiments, the distal sleeve 323 can be made of polymeric materials. The distal sleeve 323 can define one or more receptacles in which the one or more detent balls 326, respectively, are loosely retained.

In the depicted embodiment, the sliding collar 324 is configured to be longitudinally slidable between a proximal position and a distal position. In the distal position (as shown), the inner diameter of the sliding collar 324 makes contact with and exerts pressure to the one or more detent balls 326. Such pressure from the sliding collar 324 forces the one or more detent balls 326 radially inward so that the one or more detent balls 326 releasably engage with the distal cannula portion 360, as described further below. As the sliding collar 324 is slid proximally toward its proximal position, the inner diameter of the sliding collar 324 passes proximally over the one or more detent balls 326 so that the pressure from the inner diameter of the sliding collar 324 on the one or more detent balls 326 is relieved. While the sliding collar 324 is in its proximal position, the inner diameter of the sliding collar 324 does not force the one or more detent balls 326 into engagement with the distal cannula portion 360. Hence, while the sliding collar 324 is in its proximal position, the distal cannula portion 360 is moveable in relation to the proximal cannula portion 310.

In the depicted embodiment, the spring 328 provides a force that acts to separate the sliding collar 324 distally away from the stationary collar 322. In that manner, the spring 328 biases the sliding collar 324 toward its distal position in which the inner diameter of the sliding collar 324 makes contact with and exerts pressure to the one or more detent balls 326 to releasably latch the proximal cannula portion 310 in a particular arrangement in relation to the distal cannula portion 360. Hence, unless a user actuates the user-actuatable adjustment mechanism 320 by sliding the sliding collar 324 to its proximal position, the sliding collar 324 will be located at its distal position such that the proximal cannula portion 310 will be releasably coupled with the distal cannula portion 360. When the user actuates the user-actuatable adjustment mechanism 320 by sliding the sliding collar 324 to its proximal position, the proximal cannula portion 310 will become slidably engaged with the distal cannula portion 360 so that the overall longitudinal length of the cannula assembly 300 can be adjusted as desired by the user.

In the depicted embodiment, the spring 328 is a coil compression spring. In some embodiments, other types of springs can be used for the spring 328. For example, types of springs such as, but not limited to, wave springs, disc springs, and the like, can be used for the spring 328.

Figures 10, 11, 12:
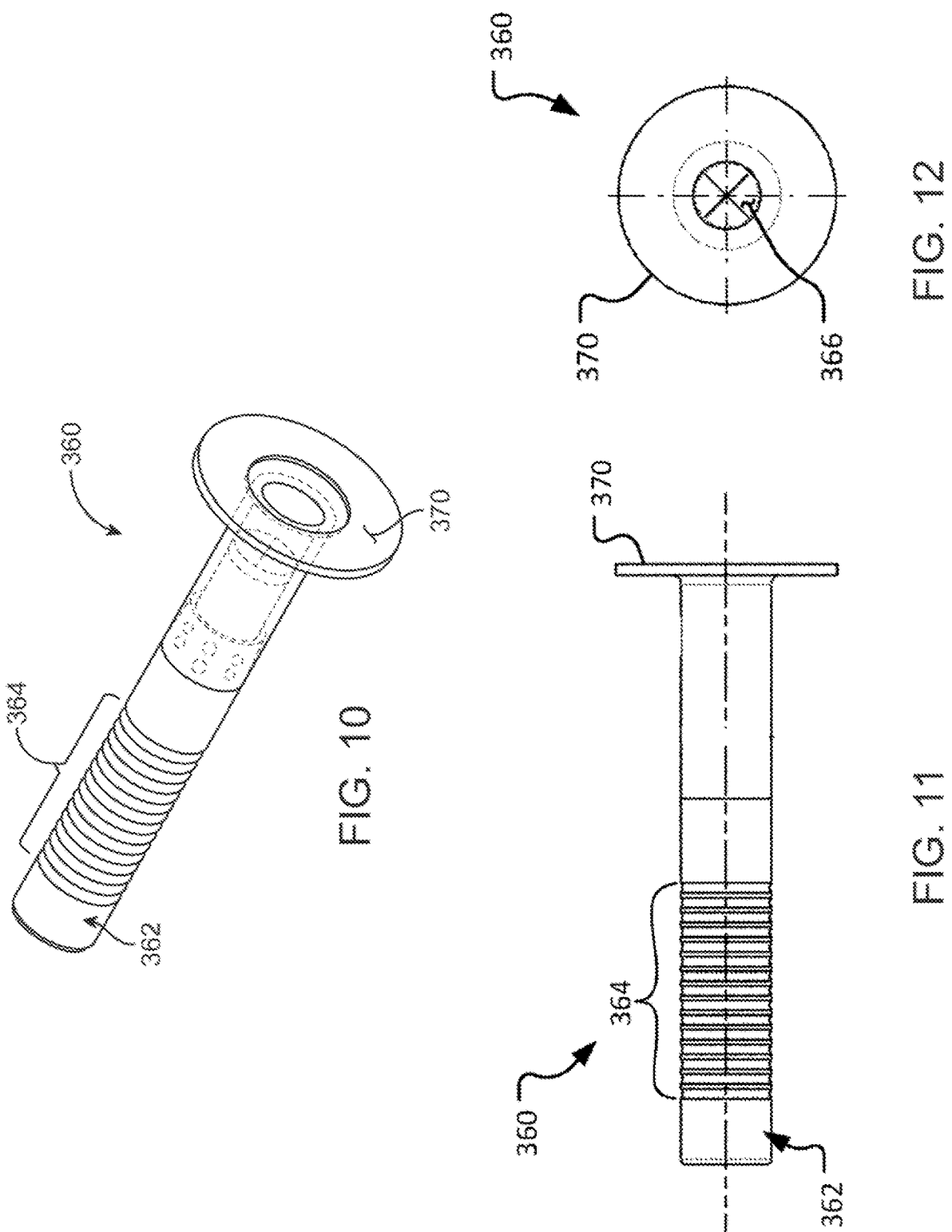
FIG. 10 is a perspective view of a distal cannula portion of the cannula assembly of FIG. 7.
FIG. 11 is a side view of the distal cannula portion of FIG. 10.
FIG. 12 is a distal end view of the distal cannula portion of FIG. 10.

Referring also to FIGS. 10-12, in the depicted embodiment the distal cannula portion 360 includes a barrel 362 and a body wall retractor 370. The body wall retractor 370 is located at the distal end portion of the barrel 362. The outer diametrical surface of the barrel 362 is configured to slidably engage within the inner diameter of the distal sleeve 323.

The barrel 362 defines a plurality of depressions 364 that are individually configured to releasably mate and engage with the one or more detent balls 326. Hence, in some embodiments the plurality of depressions 364 are radiused to approximate the shape and size of the one or more detent balls 326. In the depicted embodiment, the plurality of depressions 364 are annular grooves defined by the barrel 362.

The plurality of depressions 364 are arranged in a series, longitudinally along the length of the barrel 362. In some embodiments, the plurality of depressions 364 are separated from each other by a consistent distance. For example, in the depicted embodiment the centers of adjacent depressions 364 are each 1 mm apart from each other. Hence, the overall length of cannula assembly 300 is adjustable in 1 mm increments. In some embodiments, increments other than 1 mm are used, such as 0.5 mm, 1.5 mm, 2.0 mm, 3 mm, 4 mm, 5 mm, and the like.

In some embodiments, the barrel 362 is made of a metallic material such as, but not limited to, stainless steel, titanium, and the like. In some embodiments, the barrel 362 is made of a rigid polymeric material such as, but not limited to, polysulfone, polyether ether ketone, polysulphide, polyester, polyphenylene, polyaryletherketone, and the like, and combinations thereof.

The barrel 362 can include one or more indicator marks thereon. Such indicator marks can provide a visual indication of the overall length of the cannula assembly 300. Also, while the cannula assembly 300 is in use on a patient, the indicator marks can provide a visual indication of the amount of tenting being exerted to the body wall of the patient.

The distal cannula portion 360 also includes the body wall retractor 370. In the depicted embodiment, the body wall retractor 370 is a deflectable flange. As described further below, the body wall retractor 370 is reconfigurable between a low-profile arrangement and a diametrically expanded configuration. The low-profile arrangement is used while inserting the body wall retractor 370 through an incision in a body wall of a patient. After the body wall retractor 370 has been inserted through the incision, the body wall retractor 370 can be reconfigured to the diametrically expanded configuration. In the diametrically expanded configuration, the body wall retractor 370 is configured and operable to engage with and to exert a retraction force on the body wall (i.e., to facilitate tissue tenting of the body wall).

In the depicted embodiment, the body wall retractor 370 is a deflectable flange. To configure the deflectable flange in the low-profile arrangement, a device such as a clamp, a sleeve, a removable retention member, and/or the like can be used to removable exert a diametrical collapsing force to the deflectable flange. After the deflectable flange in the low-profile arrangement has been inserted through the body wall incision, the device can be removed so that the deflectable flange can reconfigure to the diametrically expanded configuration in preparation for engagement with the body wall. In some embodiments, the deflectable flange self-reconfigures to the diametrically expanded configuration. In some embodiments, the deflectable flange is reconfigurable to the diametrically expanded configuration when one or more forces are applied thereto by a clinician-operator.

While in the depicted embodiment, the body wall retractor 370 is a deflectable flange, other types of body wall retractors 370 are also envisioned and within the scope of this disclosure. For example, in some embodiments the body wall retractor 370 can be, without limitation, an inflatable member, a shape-memory member (e.g., one or more members comprising a material such as Nitinol), an expandable member that is radially deployable by a compressive force, and the like.

In the depicted embodiment, the body wall retractor 370 can be made of a resilient material such as, but not limited to, silicone (e.g., about shore 60A, or in a range from about shore 40A to about 80A), or another type of soft, medium-soft, or medium-rigid polymer. In some embodiments, the body wall retractor 370 is overmolded onto the barrel 362.

In some embodiments, the distal cannula portion 360 also includes a seal 366 within the lumen of the distal cannula portion 360. Such a seal 366 can serve to occlude the lumen of the distal cannula portion 360 while no surgical instruments are disposed therein. Accordingly, the seal 366 may provide resistance to fluids that might otherwise pass through the lumen of the distal cannula portion 360. The seal 366 can be deflectable such that when a surgical instrument is slid into the lumen of the distal cannula portion 360, the seal 366 will be deflected to allow the surgical instrument to pass through the seal 366, and through the lumen of the distal cannula portion 360. Thereafter, the seal 366 may provide resistance to fluids from passing through the lumen of the distal cannula portion 360 while the surgical instrument is disposed therein.

Figures 13, 14:
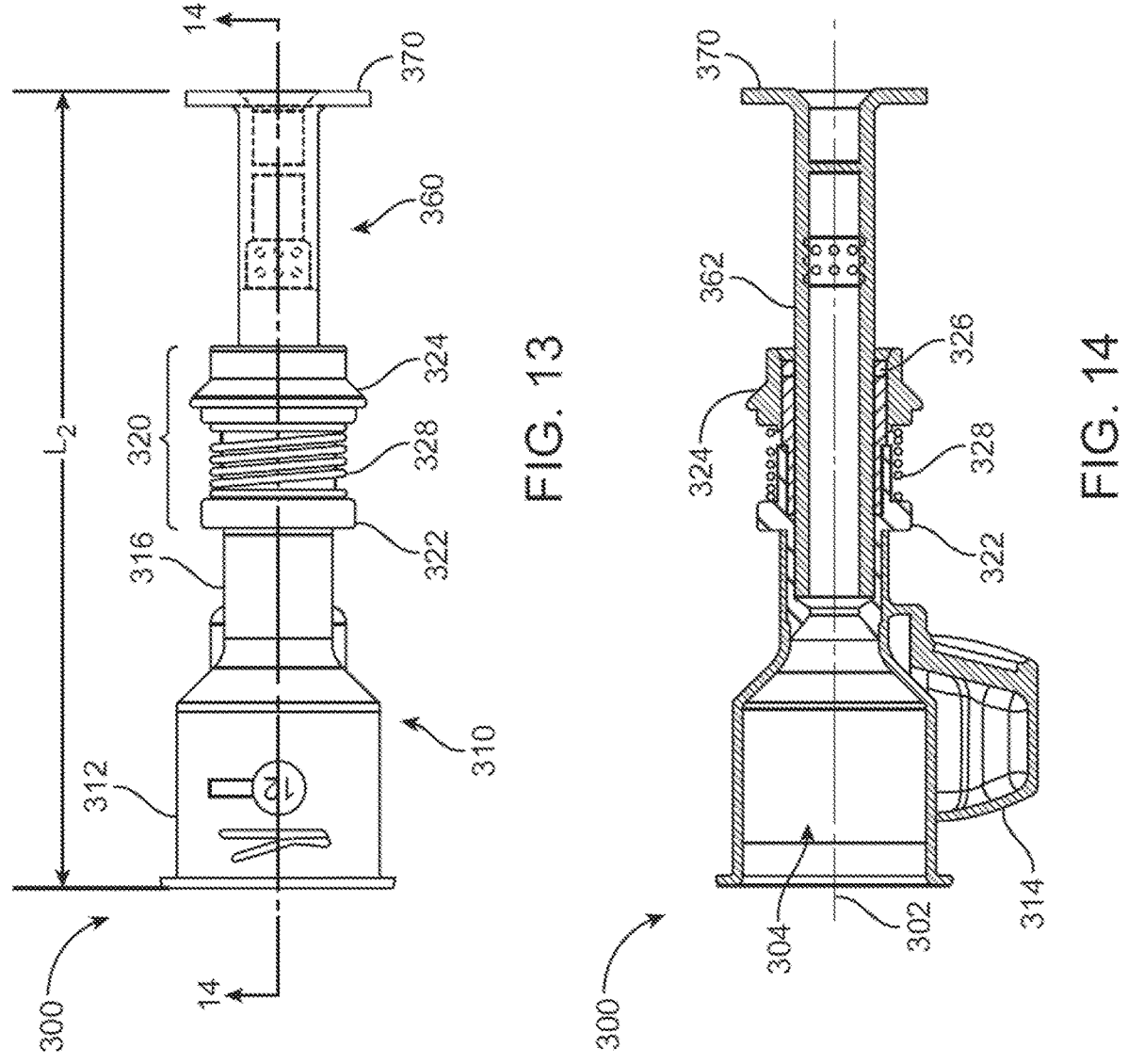
FIG. 13 is a side view of the cannula assembly of FIG. 7. In this view, the distal cannula portion is in a retracted arrangement in relation to the proximal cannula portion.
FIG. 14 is a longitudinal cross-sectional view of the cannula assembly of FIG. 13.

Referring also to FIGS. 13 and 14, the overall length of the cannula assembly 300 is adjustable during use. For example, while the arrangement of the cannula assembly 300 in FIGS. 7 and 9 has an overall length $L_1$, the arrangement of the cannula assembly 300 in FIGS. 13 and 14 has an overall length $L_2$. The overall length $L_1$ is greater than the overall length $L_2$. A clinician-user can adjust the overall length of the cannula assembly 300 from $L_1$ to $L_2$ (or vice-versa), and to various lengths between $L_1$ and $L_2$.

In the arrangement of FIGS. 7 and 9, the overall length $L_1$ is maximized because the one or more detent balls 326 is/are engaged with the proximal-most depression of the plurality of depressions 364 on the distal cannula portion 360. In the arrangement of FIGS. 13 and 14, the overall length $L_2$ is minimized because the one or more detent balls 326 is/are engaged with the distal-most depression of the plurality of depressions 364 on the distal cannula portion 360. Various lengths of the cannula assembly between lengths $L_1$ and $L_2$ are attainable by engaging the one or more detent balls 326 with any of the depressions of the plurality of depressions 364 between the proximal-most depression and the distal-most depression.

In some embodiments, the adjustability of the length of the cannula assembly 300 (the difference between lengths $L_1$ and $L_2$) is in a range of about 0.5 cm to about 2.5 cm, or about 0.7 cm to about 2.0 cm, or about 0.9 cm to about 1.8 cm, or about 1.2 cm to about 1.6 cm. In some embodiments, the adjustability of the length of the cannula assembly 300 is in a range of about 1.0 cm to about 2.0 cm, or about 1.2 cm to about 1.8 cm, or about 1.4 cm to about 1.6 cm, or about 1.0 cm to about 1.6 cm.

To adjust the overall longitudinal length of the cannula assembly 300, a clinician-user can perform the following steps. First, the clinician-user can push and hold the sliding collar 324 toward the stationary collar 322. Doing so will compress the spring 328. Therefore, the clinician-user will need to sustain force on the sliding collar 324 to maintain the sliding collar 324 in a position near to the stationary collar 322 (otherwise the spring 328 will return the sliding collar 324 distally to its at rest position). While the sliding collar 324 is positioned near the stationary collar 322, the radially-inward force exerted by the inner diameter of the sliding collar 324 on the one or more detent balls 326 is relieved. In turn, the one or more detent balls 326 is/are allowed to disengage from a depression of the plurality of depressions 364. Then, the clinician-user can slide the distal cannula portion 360 proximally and/or distally in relation to the proximal cannula portion 310 to attain the desired overall length of the cannula assembly 300. The sliding of the distal cannula portion 360 proximally and/or distally in relation to the proximal cannula portion 310 is reminiscent of tele-scopic motion. When the desired overall length of the cannula assembly 300 is attained, then the clinician-user can release the sliding collar 324 and the spring 328 will return the sliding collar 324 to its at rest position. In turn, a radially-inward force will be once again exerted by the inner diameter of the sliding collar 324 on the one or more detent balls 326, and the one or more detent balls 326 will become engaged with a particular depression of the plurality of depressions 364. Accordingly, the user-actuatable adjust-ment mechanism 320 will latch the distal cannula portion 360 in a particular position relative to the proximal cannula portion 310.

In some cases, the body wall retractor 370 is within the patient (i.e., at an internal side of a body wall of the patient) during the adjustment of the overall longitudinal length of the cannula assembly 300. In such a case, shortening the overall longitudinal length of the cannula assembly 300 may result in tenting of the patient's body wall. Such tenting can advantageously increase the internal surgical workspace within the patient.

In some cases, the remote center of motion (RCM) of the robotic surgery manipulator arm to which the cannula assembly 300 is attached is maintained unchanged even though the overall longitudinal length of the cannula assem-bly 300 has been shortened to create a body wall tent. In one non-limiting example, the RCM can be located about at the position of the seal 366 while the cannula assembly 300 is arranged to have its maximum length $L_1$. Then, during and after adjustment to shorten the overall length of the cannula assembly 300 to create a body wall tent, the RCM can remain at the same point in space (while the seal 366 will be located proximal of the RCM). In some such cases, the RCM will be located about at the position of the body wall retractor 370 while the cannula assembly 300 is arranged to have its minimum length $L_2$.

In some cases, the RCM of the robotic surgery manipu-lator arm to which the cannula assembly 300 is attached is adjusted in correspondence to the change in the overall longitudinal length of the cannula assembly 300 that has been shortened to create a body wall tent. In some cases, the RCM of the robotic surgery manipulator arm to which the cannula assembly 300 is attached will be located distally of the body wall retractor 370 while the body wall is tented by the body wall retractor 370.

Referring to FIGS. 15-18, another example cannula assembly 400 includes a proximal cannula portion 410 and a distal cannula portion 460. In some cases, the cannula assembly 400 may also be referred to as a "trocar." The cannula assembly 400 defines a longitudinal axis 402 and a lumen 404 extending longitudinally through each of the proximal cannula portion 410 and the distal cannula portion 460. The lumen 404 is configured to slidably receive the shaft of a surgical instrument, such as the surgical instrument 200 described above.

In the depicted embodiment, the distal cannula portion 460 is adjustably engaged with the proximal cannula portion 410. That is, as described further below, the position of the distal cannula portion 460 in relation to the proximal can-nula portion 410 is user-adjustable. Such adjustability of the distal cannula portion 460 in relation to the proximal can-nula portion 410 facilitates the ability to adjust the overall longitudinal length of the cannula assembly 400 and to tent a body wall, as described further below.

Proximal cannula portion 410 includes a cannula bowl 412, an attachment member 414, a throat 416, and a user-actuatable adjustment mechanism 420. In some embodi-ments, the cannula bowl 412, the attachment member 414, and the throat 416 can be constructed like a conventional cannula for robotic surgery. The attachment member 414 is configured to releasably couple with the cannula clamp 126 (FIG. 3). The adjustment mechanism 420 is coupled to the throat 416.

In the depicted embodiment, the user-actuatable adjust-ment mechanism 420 includes a stationary collar 422, a distal sleeve 423, and a latch mechanism 424. The user-actuatable adjustment mechanism 420 releasably couples the distal cannula portion 460 in a particular longitudinal relationship with the proximal cannula portion 410. The latch mechanism 424 can be actuated by a clinician-user to allow adjustment of the overall length of the cannula assem-bly 400, as described further below. Such adjustment of the overall length of the cannula assembly 400 can be used to tent a body wall thereby increasing a size of a surgical workspace.

In the depicted embodiment, the stationary collar 422 is coupled to the throat 416. The distal sleeve 423 is coupled to the stationary collar 422. The latch mechanism 424 is captured between the distal sleeve 423 and the stationary collar 422.

In some embodiments, the distal sleeve 423 can be made of a material that provides low sliding friction in relation to the distal cannula portion 460. For example, in some embodiments the distal sleeve 423 can be made of metallic materials such as, but not limited to, bronze, brass, stainless steel, impregnated metals, coated metals, and the like. In some embodiments, the distal sleeve 423 can be made of polymeric materials.

The latch mechanism 424 can be implemented in many different designs. In the depicted embodiment, the latch mechanism 424 includes opposing buttons 425a and 425b. Each button 425a and 425b is coupled with a radially-inward projecting tooth 426a and 426b, respectively. When the button 425a is depressed radially-inward by a clinician-user, the tooth 426a moves radially-outward by the same distance that the button 425a is moved radially-inward. Likewise, when the button 425b is depressed radially-inward by a clinician-user, the tooth 426b moves radially-outward by the same distance that the button 425b is moved radially-inward. It follows that if the clinician-user depresses the opposing buttons 425a and 425b concurrently, the teeth 426a and 426b move radially-outward concurrently. When the teeth 426a and 426b move radially-outward, the teeth 426a and 426b disengage from depressions on the distal cannula portion 460, allowing the distal cannula portion 460 to be slid longitudinally in relation to the proximal cannula portion 410.

The latch mechanism 424 can include one or more springs that bias the buttons 425a and 425b to their radially-outward rest positions (such that the teeth 426a and 426b are positioned radially-inward where the teeth 426a and 426b may engage with the distal cannula portion 460). Hence, unless a user actuates the user-actuatable adjustment mechanism 420 by depressing the buttons 425a and 425b, the teeth 426a and 426b will be releasably coupled with the distal cannula portion 460. When the user actuates the user-actuatable adjustment mechanism 420 by simultaneously depressing the buttons 425a and 425b, the teeth 426a and 426b will each disengage from the distal cannula portion 460 and the distal cannula portion 460 will become slidably engaged with the proximal cannula portion 410 so that the overall longitudinal length of the cannula assembly 400 can be adjusted as desired by the user.

While in the depicted embodiment the latch mechanism 424 includes opposing buttons 425a and 425b that actuate radially-inward projecting teeth 426a and 426b, in some embodiments other types of latch mechanisms are used. In some embodiments, a ratcheting mechanism can be used for the latch mechanism 424. In some such cases a knob, lever, removable tool, and/or the like can be used to adjust the overall length of the cannula assembly 400 by manipulating the ratcheting mechanism. In some embodiments, a threaded arrangement between the proximal cannula portion 410 and the distal cannula portion 460 can be included. In some embodiments, one or more gears (e.g., a rack and pinion arrangement) can be included as part of the latch mechanism 424. It should be recognized that all such mechanisms, and others, are included in the scope of this disclosure.

Figures 19, 20, 21:
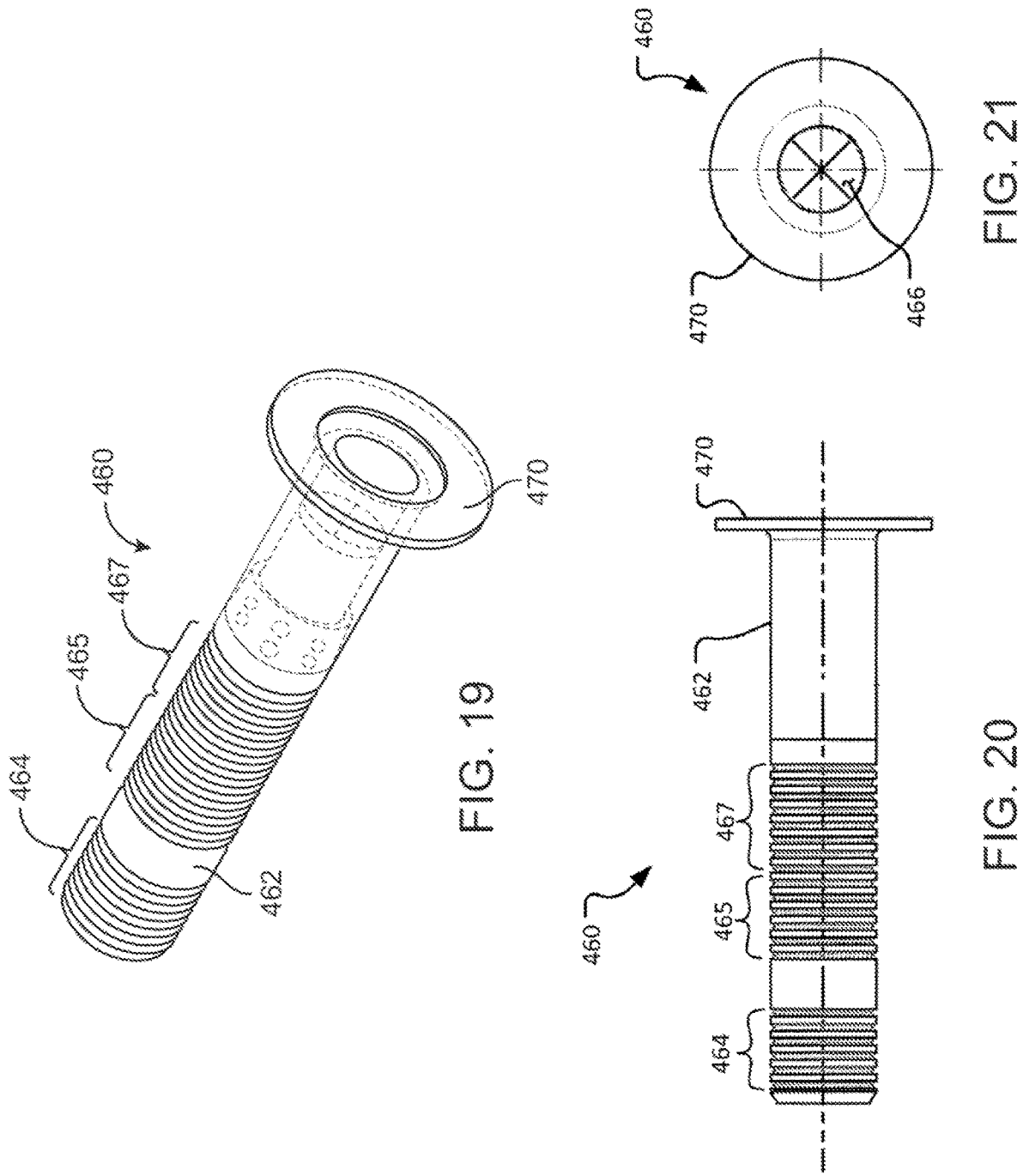
FIG. 19 is a perspective view of a distal cannula portion of the cannula assembly of FIG. 15.
FIG. 20 is a side view of the distal cannula portion of FIG. 19.
FIG. 21 is a distal end view of the distal cannula portion of FIG. 19.

Referring also to FIGS. 19-21, in the depicted embodiment the distal cannula portion 460 includes a barrel 462 and a body wall retractor 470. The body wall retractor 470 is located at the distal end portion of the barrel 462. The outer diametrical surface of the barrel 462 is configured to slidably engage within the inner diameter of the distal sleeve 423.

The barrel 462 defines a plurality of depressions 464 that are individually configured to releasably mate and engage with the radially-inward projecting teeth 426a and 426b. Hence, in some embodiments the plurality of depressions 464 are shaped to approximate the shape and size of the radially-inward projecting teeth 426a and 426b. In the depicted embodiment, the plurality of depressions 464 are annular grooves defined by the barrel 462.

The plurality of depressions 464 are arranged in a series, longitudinally along the length of the barrel 462. In some embodiments, the plurality of depressions 464 are separated from each other by a consistent distance. For example, in the depicted embodiment the centers of adjacent depressions 464 are each 1 mm apart from each other. Hence, the overall length of cannula assembly 400 is adjustable in 1 mm increments. In some embodiments, increments other than 1 mm are used, such as 0.5 mm, 1.5 mm, 2.0 mm, 4 mm, 4 mm, 5 mm, and the like.

In some embodiments, the barrel 462 is made of a metallic material such as, but not limited to, stainless steel, titanium, and the like. In some embodiments, the barrel 462 is made of a rigid polymeric material such as, but not limited to, polysulfone, polyether ether ketone, polysulphide, polyester, polyphenylene, polyaryletherketone, and the like, and combinations thereof.

The barrel 462 can include one or more indicator marks 465 thereon. Such indicator marks 465 can provide a visual indication of the overall length of the cannula assembly 400. Also, while the cannula assembly 400 is in use on a patient, the indicator marks 465 can provide a visual indication of the amount of tenting being exerted to the body wall of the patient.

The barrel 462 can also include one or more regions of surface texturing 467. The surface texturing 467 can be grooves (as shown), knurling, dimples, projections, and the like. The surface texturing 467 can facilitate secure gripping of the barrel 462 by the user.

The distal cannula portion 460 also includes the body wall retractor 470. In the depicted embodiment, the body wall retractor 470 is a deflectable flange. The body wall retractor 470 is reconfigurable between a low-profile arrangement and a diametrically expanded configuration. The low-profile arrangement is used while inserting the body wall retractor 470 through an incision in a body wall of a patient. After the body wall retractor 470 has been inserted through the incision, the body wall retractor 470 can be reconfigured to the diametrically expanded configuration as shown. In the diametrically expanded configuration, the body wall retractor 470 is configured and operable to engage with and to exert a retraction force on the body wall (i.e., to facilitate tissue tenting of the body wall).

In the depicted embodiment, the body wall retractor 470 is a deflectable flange. To configure the deflectable flange in the low-profile arrangement, a device such as a clamp, a sleeve, a removable retention member, and/or the like can be used to removable exert a diametrical collapsing force to the deflectable flange. After the deflectable flange in the low-profile arrangement has been inserted through the body wall incision, the device can be removed so that the deflectable flange can reconfigure to the diametrically expanded configuration in preparation for engagement with the body wall. In some embodiments, the deflectable flange self-reconfigures to the diametrically expanded configuration. In some embodiments, the deflectable flange is reconfigurable to the diametrically expanded configuration when one or more forces are applied thereto by a clinician-operator.

While in the depicted embodiment, the body wall retractor 470 is a deflectable flange, other types of body wall retractors 470 are also envisioned and within the scope of this disclosure. For example, in some embodiments the body wall retractor 470 can be, without limitation, an inflatable member, a shape-memory member (e.g., one or more members comprising a material such as nitinol), an expandable member that is radially deployable by a compressive force, and the like.

In the depicted embodiment, the body wall retractor 470 can be made of a resilient material such as, but not limited to, silicone (e.g., about shore 60A, or in a range from about shore 40A to about 80A), or another type of soft, medium-soft, or medium-rigid polymer. In some embodiments, the body wall retractor 470 is overmolded onto the barrel 462.

In some embodiments, the distal cannula portion 460 also includes a seal 466 within the lumen of the distal cannula portion 460. Such a seal 466 can serve to occlude the lumen of the distal cannula portion 460 while no surgical instruments are disposed therein. Accordingly, the seal 466 may provide resistance to fluids that might otherwise pass through the lumen of the distal cannula portion 460. The seal 466 can be deflectable such that when a surgical instrument is slid into the lumen of the distal cannula portion 460, the seal 466 will be deflected to allow the surgical instrument to pass through the seal 466, and through the lumen of the distal cannula portion 460. Thereafter, the seal 466 may provide resistance to fluids from passing through the lumen of the distal cannula portion 460 while the surgical instrument is disposed therein.

Referring also to FIGS. 22-25, the overall length of the cannula assembly 400 is adjustable during use. For example, while the arrangement of the cannula assembly 400 in FIGS. 15, 16, and 18 has an overall length $L_1$, the arrangement of the cannula assembly 400 in FIGS. 22, 23, and 25 has an overall length $L_2$. The overall length $L_1$ is greater than the overall length $L_2$. A clinician-user can adjust the overall length of the cannula assembly 400 from $L_1$ to $L_2$ (or vice versa), and to various lengths between $L_1$ and $L_2$.

Figures 15, 16, 17, 18:
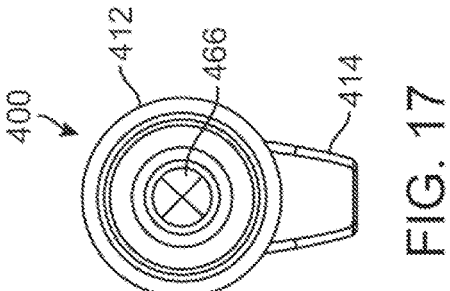
FIG. 15 is a side view of another exemplary cannula assembly with a flanged distal end for facilitating creation of a tissue tent during computer-assisted tele-operated surgery. The cannula assembly includes a proximal cannula portion and a distal cannula portion. In this view, the distal cannula portion is in an extended arrangement in relation to the proximal cannula portion.
FIG. 16 is another side view of the cannula assembly of FIG. 15.
FIG. 17 is a proximal end view of the cannula assembly of FIG. 15.
FIG. 18 is a longitudinal cross-sectional view of the cannula assembly of FIG. 15.

In the arrangement of FIGS. 15, 16, and 18, the overall length $L_1$ is maximized because teeth 426a and 426b are engaged with the proximal-most depression of the plurality of depressions 464 on the distal cannula portion 460. In the arrangement of FIGS. 22, 23, and 25, the overall length $L_2$ is minimized because the teeth 426a and 426b are engaged with the distal-most depression of the plurality of depressions 464 on the distal cannula portion 460. Various lengths of the cannula assembly between lengths $L_1$ and $L_2$ are attainable by engaging the teeth 426a and 426b with any of the depressions of the plurality of depressions 464 between the proximal-most depression and the distal-most depression.

In some embodiments, the adjustability of the length of the cannula assembly 400 (the difference between lengths $L_1$ and $L_2$) is in a range of about 0.5 cm to about 2.5 cm, or about 0.7 cm to about 2.0 cm, or about 0.9 cm to about 1.8 cm, or about 1.2 cm to about 1.6 cm. In some embodiments, the adjustability of the length of the cannula assembly 400 is in a range of about 0.5 cm to about 1.5 cm, or about 0.7 cm to about 1.3 cm, or about 0.8 cm to about 1.2 cm, or about 0.9 cm to about 1.1 cm.

To adjust the overall longitudinal length of the cannula assembly 400, a clinician-user can perform the following steps. First, the clinician-user can depress and hold the opposing buttons 425a and 425b. Doing so will compress the spring(s) that biases the opposing buttons 425a and 425b to their radially-outward rest positions. Therefore, the clinician-user will need to sustain force on the opposing buttons 425a and 425b to maintain the opposing buttons 425a and 425b in their radially-inward depressed positions (otherwise the spring(s) will return the opposing buttons 425a and 425b to their rest positions). While the opposing buttons 425a and 425b are depressed, the teeth 426a and 426b will disengage from one or more depressions of the plurality of depressions 464. Then, the clinician-user can slide the distal cannula portion 460 proximally and/or distally in relation to the proximal cannula portion 410 to attain the desired overall length of the cannula assembly 400. The sliding of the distal cannula portion 460 proximally and/or distally in relation to the proximal cannula portion 410 is reminiscent of telescopic motion. When the desired overall length of the cannula assembly 400 is attained, then the clinician-user can release the opposing buttons 425a and 425b and the spring(s) will return the opposing buttons 425a and 425b to their radially-outward rest positions. In turn, a radially-inward force will be once again exerted by the teeth 426a and 426b, and the teeth 426a and 426b will become engaged with one or more particular depressions of the plurality of depressions 464. Accordingly, the user-actuatable adjustment mechanism 420 will latch the distal cannula portion 460 in a particular position relative to the proximal cannula portion 410.

In some cases, the body wall retractor 470 is within the patient (i.e., at an internal side of a body wall of the patient) during the adjustment of the overall longitudinal length of the cannula assembly 400. In such a case, shortening the overall longitudinal length of the cannula assembly 400 may result in tenting of the patient's body wall. Such tenting can advantageously increase the internal surgical workspace within the patient.

In some cases, the remote center of motion (RCM) of the robotic surgery manipulator arm to which the cannula assembly 400 is attached is maintained unchanged even though the overall longitudinal length of the cannula assembly 400 has been shortened to create a body wall tent. In one non-limiting example, the RCM can be located about at the position of the seal 466 while the cannula assembly 400 is arranged to have its maximum length $L_1$. Then, during and after adjustment to shorten the overall length of the cannula assembly 400 to create a body wall tent, the RCM can remain at the same point in space (while the seal 466 will be located proximal of the RCM). In some such cases, the RCM will be located about at the position of the body wall retractor 470 while the cannula assembly 400 is arranged to have its minimum length $L_2$.

In some cases, the RCM of the robotic surgery manipulator arm to which the cannula assembly 400 is attached is adjusted in correspondence to the change in the overall longitudinal length of the cannula assembly 400 that has been shortened to create a body wall tent. In some cases, the RCM of the robotic surgery manipulator arm to which the cannula assembly 400 is attached will be located distally of the body wall retractor 470 while the body wall is tented by the body wall retractor 470.

Figure 26:
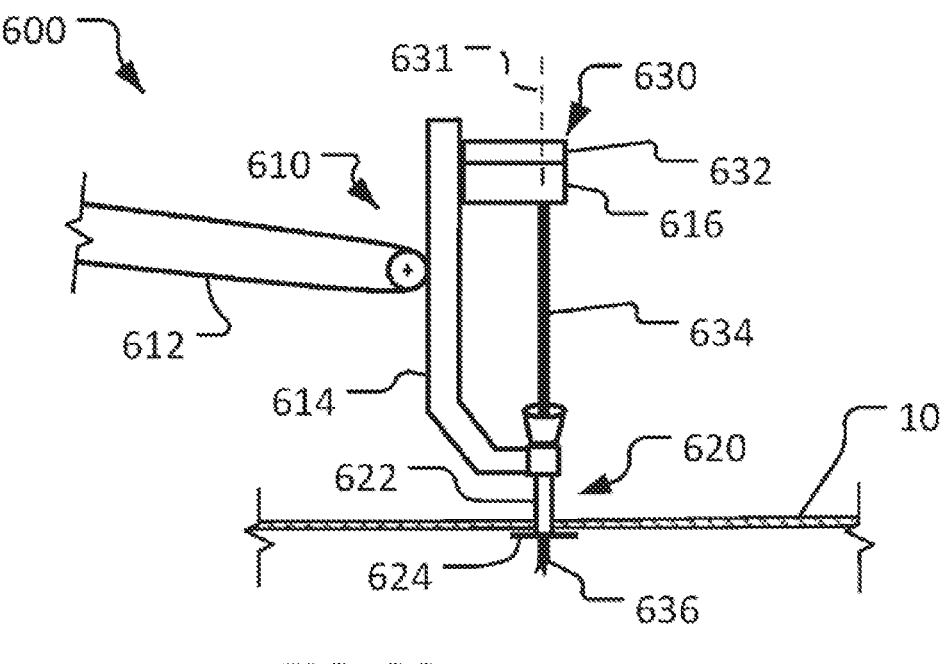
FIGS. 26 and 27 illustrate an example method for implementing body wall tenting using the devices provided herein.
Figure 27:
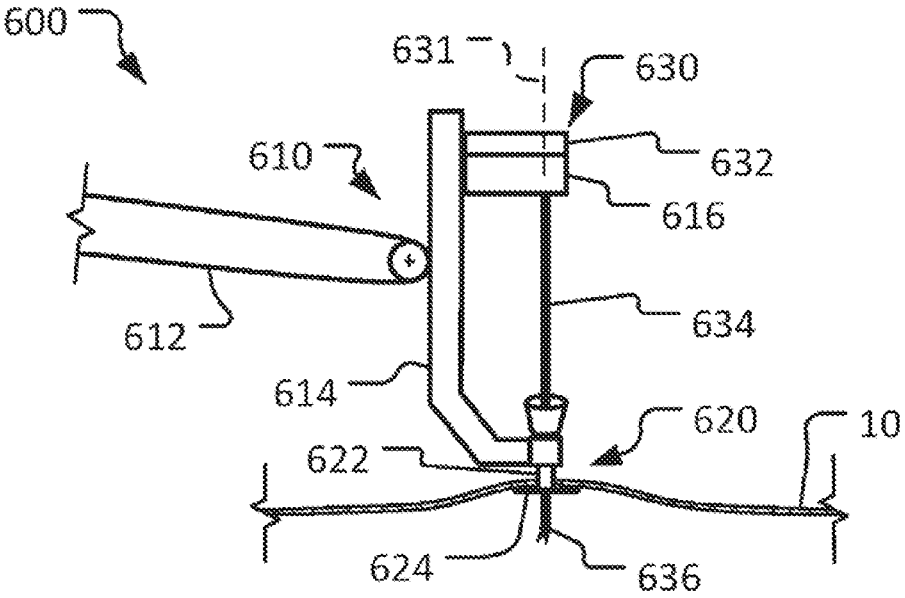
Figure 28:
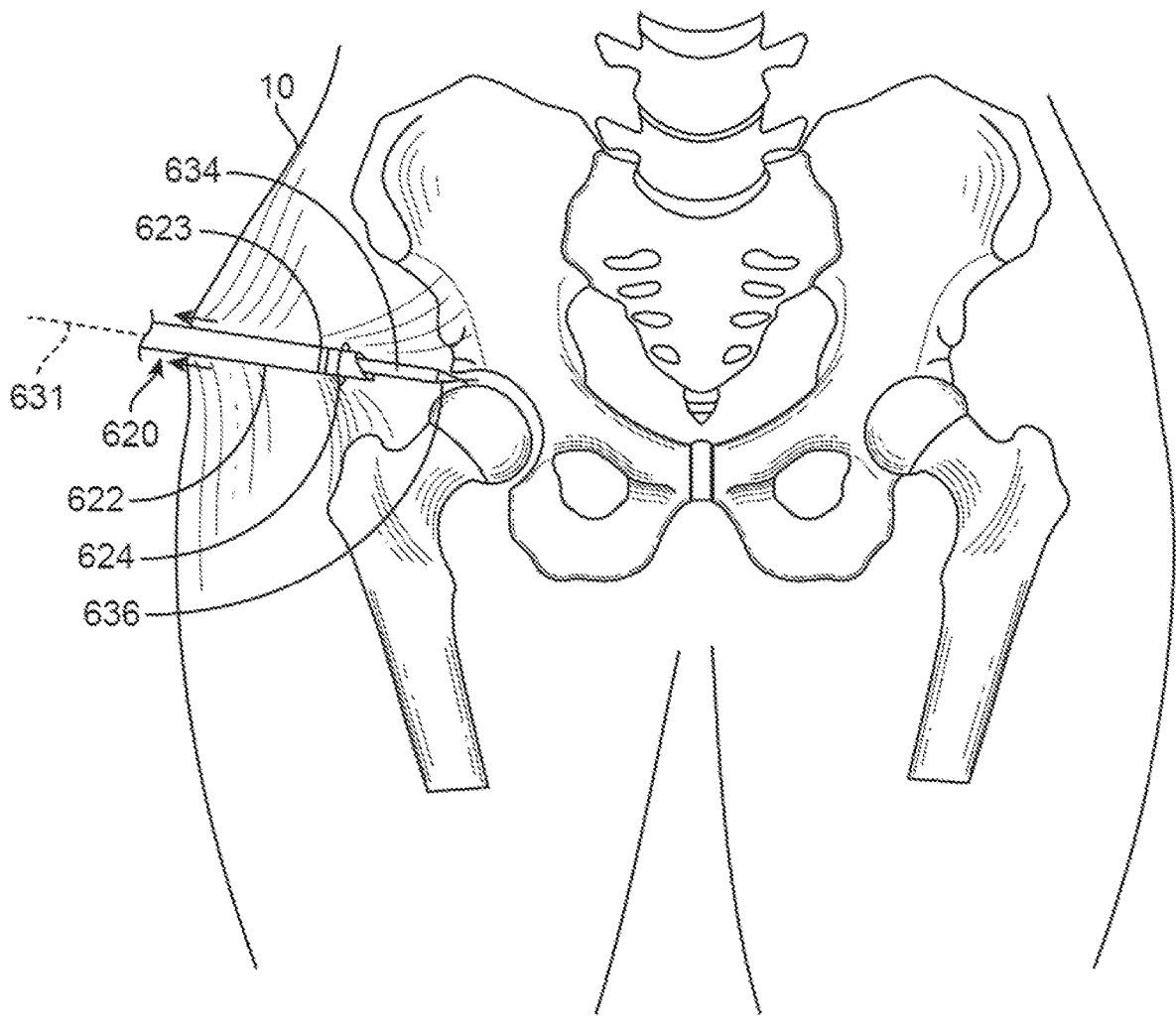
FIG. 28 illustrates a method of tenting a body wall in the context of a minimally invasive robotic surgery on a hip joint using the devices provided herein.

Referring to FIGS. 26-28, a surgical system 600 can be used to perform a minimally invasive robotic surgical method. The surgical system 600 is a portion of a robotic surgery patient-side cart (like the patient side cart 100 of FIG. 1, for example). In this example, the surgical system 600 is used to tent an outer tissue layer 10 (e.g., body wall), thereby creating a larger surgical working space below the outer tissue layer 10. By creating a larger working space within the patient, increased surgical access and better visibility for the minimally invasive surgery can be advantageously attained. FIG. 26 shows the surgical system 600 prior to tenting the outer tissue layer 10. FIG. 27 shows the surgical system 600 after tenting the outer tissue layer 10. In some implementations, the outer tissue layer 10 is the outer body wall (outer skin, muscle, fat, etc.) of a patient through which an incision is made to access the target operative area.

The surgical system 600 includes a robotic manipulator arm assembly 610, a cannula 620, and a surgical instrument 630. The robotic manipulator arm assembly 610 includes a robotic manipulator arm 612 and an instrument holder 614. The instrument holder 614 is pivotably coupled to the robotic manipulator arm 612. The cannula 620 is releasably coupled to the instrument holder 614. The surgical instrument 630 is releasably coupled to an instrument holder carriage 616 that is controllably translatable along the instrument holder 614.

The surgical instrument 630 includes a transmission assembly 632 that is releasably coupleable with the instrument holder carriage 616. The surgical instrument 630 includes an elongate shaft 634 that extends from the transmission assembly 632. At the distal end of the elongate shaft 634 is an end effector 636. A variety of alternative robotic surgical instruments 630 of different types and differing end effectors 636 may be used, with the instruments sometimes being removed and replaced during a surgical procedure.

The cannula 620 defines a lumen in which the elongate shaft 634 is slidably coupled. As the instrument holder carriage 616 is translated along the instrument holder 614, the instrument 630 moves along with the instrument holder carriage 616. Consequently, the elongate shaft 634 slides within the lumen of the cannula 620. Hence, the elongate shaft 634 (and the end effector 636) becomes extended distally and/or retracted proximally in relation to the cannula 620 by translational movements of the instrument holder carriage 616 along the instrument holder 614. In such a fashion, the end effector 636 can be moved distally deeper into the operative space, or moved proximally away from the operative space. However, such a translation of the instrument holder carriage 616, and the instrument 630, does not involve any movement of the cannula 620.

The elongate shaft 634 defines a longitudinal axis 631. As the instrument holder carriage 616 is translated along the instrument holder 614, the instrument 630 is moved along the longitudinal axis 631.

The cannula 620 includes a cannula shaft 622 and a body wall retractor 624. The body wall retractor 624 is coupled to a distal end of the cannula shaft 622. The body wall retractor 624 is reconfigurable between a low-profile delivery configuration and a diametrically expanded, deployed configuration. The low-profile configuration of the body wall retractor 624 can be used, for example, while inserting or removing the cannula 620 through an incision in the outer tissue layer 10 the patient.

In use, the cannula shaft 622 is inserted through an incision in the outer tissue layer 10 such that the body wall retractor 624 is positioned below the outer tissue layer 10 (i.e., within the patient). After passing the body wall retractor 624 generally through the outer tissue layer 10, the body wall retractor 624 can be coupled with the outer tissue layer 10. For example, in the depicted embodiment the body wall retractor 624 can be diametrically expanded in preparation for tenting the outer tissue layer 10. Then, to tent the outer tissue layer 10, the body wall retractor 624 is moved away from the patient (as depicted by FIG. 27 in comparison to FIG. 26, and as depicted in FIG. 28).

To tent the outer tissue layer 10 as depicted in FIGS. 27 and 28, the overall length of the cannula 620 is shortened (while the body wall retractor 624 coupled with the outer tissue layer 10). To accomplish such a shortening adjustment, the overall length of the cannula 620 can be shortened by a clinician-user such as by the techniques described above in reference to cannula assemblies 300 and/or 400. As the overall length of the cannula 620 is shortened, the position of the robotic manipulator arm assembly 610, including the robotic manipulator arm 612 and the instrument holder 614, can be maintained stationary. In some embodiments, such as the depicted embodiment, the body wall retractor 624 is moved away from the patient along a fixed line in space that is coincident with the longitudinal axis 631.

Tenting of the outer tissue layer 10 may be particularly advantageous for robotic surgeries in locations of the body that have shallow surgical working spaces. Said differently, tenting of the outer tissue layer 10 may be particularly advantageous for robotic surgeries in locations of the body where the entry point through the outer tissue layer 10 is close to the operative point/area.

One non-limiting example of a robotic surgery that has an entry point through the outer tissue layer 10 is close to the operative point/area is shown in FIG. 28. Here, a hip surgery is being performed using the devices, systems, and methods provided herein. That is, the body wall retractor 624 attached to the cannula shaft 622 is being pulled outward from the patient (by shortening the cannula 620) to create a larger surgical working space within the patient near the ball and socket joint of the hip.

In some cases, the RCM of the robotic surgery manipulator arm 610 to which the cannula assembly 620 is attached is maintained unchanged even though the overall longitudinal length of the cannula assembly 620 has been shortened to create a body wall tent. In one non-limiting example, during and after adjustment to shorten the overall length of the cannula assembly 620 to create a body wall tent, the RCM can remain at the same point in space. In some such cases, the RCM will be located about at the position of the body wall retractor 624 while the cannula assembly 620 is arranged to tent the outer tissue layer 10 (as depicted in FIGS. 27 and 28).

In some cases, the RCM of the robotic surgery manipulator arm 610 to which the cannula assembly 620 is attached is adjusted in correspondence to the change in the overall longitudinal length of the cannula assembly 620 that has been shortened to create a body wall tent. In some cases, the RCM of the robotic surgery manipulator arm to which the cannula assembly 610 is attached will be located distally of the body wall retractor 624 while the body wall is tented by the body wall retractor 624.

In some embodiments, one or more safety features can be used in conjunction with the techniques for controlling motions of the robotic manipulator, cannula, and surgical instrument in the various surgical contexts that are described in this disclosure. For example, in some embodiments the location of the software-constrained or hardware-constrained RCM is monitored. The location can be constrained to a limit distance away from the body wall retractor for example, and/or an alert to the surgeon can be provided when the RCM location is beyond a threshold distance.

In some embodiments, a camera can be used on the outside of the patient so that the surgeon can see the extent of the tissue tenting. For example, in some embodiments a picture-in-picture can be used with the display 45 at the surgeon console 40 (FIG. 2). That is, a video picture of the tenting taken by the camera on the outside of the patient can be fed to the display 45 of the surgeon console 40 while still allowing the surgeon to see the images from the endoscope being used for the surgery.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A medical device comprising:

a cannula assembly comprising a proximal cannula portion, a distal cannula portion and a user-actuatable adjustment mechanism configured to adjust a position of the distal cannula portion relative to the proximal cannula portion;

wherein the proximal cannula portion is configured to be releasably coupled to a computer-assisted teleoperated surgery manipulator arm;

wherein the distal cannula portion and the proximal cannula portion engaged together define a central lumen configured for slidably receiving a surgical instrument and define an overall assembly length of the cannula assembly and the central lumen along a longitudinal axis defined by the central lumen and wherein the user-actuatable adjustment mechanism comprises:

a stationary collar fixed to the proximal cannula portion, a sliding collar configured to move relative to the distal cannula portion and the proximal cannula portion, and a spring disposed between the stationary collar and the sliding collar, the spring exerting a biasing force biasing the sliding collar into a first position, wherein in the first position of the sliding collar, the sliding collar exerts a latching force releasably latching the distal cannula portion in a fixed position relative to the proximal cannula portion, wherein the sliding collar is movable away from the first position and toward the stationary collar in response to a force sufficient to overcome the biasing force of the spring, and wherein in a position of the sliding collar moved away from the first position toward the stationary collar, the latching force exerted by the sliding collar is released and the distal cannula portion is moveable relative to the proximal cannula portion and the sliding collar to adjust the overall assembly length of the cannula assembly and central lumen along the longitudinal axis.

2. The medical device of claim 1, wherein in the position of the sliding collar moved away from the first position toward the stationary collar the overall assembly length of the cannula assembly is adjustable by sliding the distal cannula portion in relation to the proximal cannula portion.

3. The medical device of claim 1, wherein:

the cannula assembly is user-adjustable into three or more different configurations; and each of the three or more different configurations defines a different length of the overall assembly length of the cannula assembly.

4. The medical device of claim 1, further comprising a seal within the central lumen in the distal cannula portion, wherein the seal is configured to provide a seal around an outer periphery of a shaft of the surgical instrument.

5. The medical device of claim 1, wherein the sliding collar surrounds a portion of the distal cannula portion.

6. The medical device of claim 1, wherein the distal cannula portion comprises a body wall retractor.

7. The medical device of claim 6, wherein the body wall retractor includes a flange.

8. The medical device of claim 7, wherein the flange is reconfigurable between an expanded unrestrained size and a smaller constrained size.

9. The medical device of claim 8, wherein the smaller constrained size is used while inserting the distal cannula portion through an incision in a body wall.

10. The medical device of claim 8, wherein the flange is resilient such that the flange self-reconfigures to the expanded unrestrained size upon removal of size-constraining forces on the flange.

11. The medical device of claim 1, further comprising at least one detent mechanism moveable between an engaged state to latch the distal cannula portion in the fixed position relative to the proximal cannula portion and a disengaged state to release the latching force on the distal cannula portion.

12. The medical device of claim 11, wherein the at least one detent mechanism comprises one or more detent members configured to be received in one or more depressions on the distal cannula portion in the engaged state.

13. The medical device of claim 11, wherein in the first position of the sliding collar, the at least one detent mechanism is in the engaged state and in the position of the sliding collar moved toward the stationary collar, the at least one detent mechanism is in the disengaged state.

14. The medical device of claim 12, wherein the one or more depressions include a plurality of depressions axially spaced from each other, the one or more detent members received in a differing depression based on the overall assembly length of the cannula assembly.

* * * * *